United States Patent
Lautenschläger

(10) Patent No.: US 8,260,735 B2
(45) Date of Patent: Sep. 4, 2012

(54) METHOD FOR ASSESSING A RUPTURE RISK OF AN ANEURYSM OF A PATIENT AND ASSOCIATED SYSTEM

(75) Inventor: Stefan Lautenschläger, Hausen (DE)

(73) Assignee: Siemens Aktiengesellschaft, München (DE)

( * ) Notice: Subject to any disclaimer, the term of this patent is extended or adjusted under 35 U.S.C. 154(b) by 1006 days.

(21) Appl. No.: 12/156,933

(22) Filed: Jun. 5, 2008

(65) Prior Publication Data

US 2009/0043187 A1   Feb. 12, 2009

(30) Foreign Application Priority Data

Jun. 8, 2007 (DE) .................. 10 2007 026 519

(51) Int. Cl.
*G06F 17/00* (2006.01)
*A61B 5/103* (2006.01)
*A61B 5/107* (2006.01)

(52) U.S. Cl. .............. 706/45; 706/21; 128/923

(58) Field of Classification Search .......... 706/45
See application file for complete search history.

(56) References Cited

U.S. PATENT DOCUMENTS

2005/0015006 A1   1/2005   Mitschke et al.
2007/0118037 A1   5/2007   Sawanoi et al.

FOREIGN PATENT DOCUMENTS

| DE | 10325003 A1 | 12/2004 |
| DE | 102005035181 A1 | 3/2006 |
| EP | 1776920 A2 | 4/2007 |
| WO | WO 2006/010609 A2 | 7/2005 |

OTHER PUBLICATIONS

Ma et al. (Ma), Three-Dimensional Geometrical Characterization of Cerebral Aneurysms. Annals of Biomedical Engineering, vol. 32, No. 2 [online], Feb. 2004 [retrieved on May 20, 2011]. Retrieved from the Internet< URL: http://www.springerlink.com/content/n45888r22372x313/fulltext.pdf>.*

Torii et al. (Torii), Fluid-structure interaction modeling of aneurysmal conditions with high and normal blood pressures. Comput. Mech. 38: 482-490 [online], 2006 [retrieved on May 20, 2011]. Retrieved from the Internet< URL:www.tafsm.org/PUB_PRE/jALL/j137-CM-HBP.pdf>.*

Raghavan et al., Quantified aneurysm shape and rupture risk. J Neurosurg 102:355-362 [online], Feb. 2005 [retrieved on Sep. 16, 2011]. Retrieved from the Internet: <URL:http://www.google.com/url?sa=t&source=web&cd=2&ved=0CCoQFjAB&url=http%3A%2F%2Fciteseerx.ist.psu.edu%2Fviewdoc%2Fdownload%3Fdoi%3D10.1.1.135.4195%26rep%3Drep1%26type%3Dpdf&ei=WwB0TvCGF-S40gGtzZTpDQ&usg=AFQjCNFxk9gGtnZOd3jMbFPiwAVCZFTIWw>.*

(Continued)

*Primary Examiner* — Jeffrey A Gaffin
*Assistant Examiner* — Nathan Brown, Jr.

(57) ABSTRACT

A method for assessing a rupture risk of at least one aneurysm of a patient, with the rupture risk being assessed by a computing device as a function of at least one personal factor specific to the patient and at least one anatomy-linked factor relevant to the anatomy of the and/or in the area of the at least one aneurysm and at least one simulation-linked factor determined with reference to at least one simulation carried out by means of the computing device and/or a further computing device and based on anatomical data for the at least one aneurysm.

12 Claims, 3 Drawing Sheets

OTHER PUBLICATIONS

Raghavan et al., Quantified aneurysm shape and rupture risk. J Neurosurg 102:355-362 [online], Feb. 2005 [retrieved on Sep. 16, 2011]. Retrieved from the internet: <URL:http://www.google.com/url?sa=web&cd=2&ved=0CCoQFjAB&url=http%3A%2F%2Fciteseerx.ist.psu.edu%2Fviewdoc%2Fdownload%3Fdoi%3D10.1.1.135.4195%26rep%3Drep1%26type%3Dpdf&ei=WwB>.*

Ma et al. (Ma), Three-Dimensional Geometrical Characterization of Cerebral Aneurysms. Annals of Biomedical Engineering, vol. 32, No. 2 [online], Feb. 2004 [retrieved on May 20, 2011]. Retrieved from the Internet<URL: http://www.springerlink.com/content/n45888r22372x313/fulltext.pdf>.*

Torii et al. (Torii), Fluid-structure interaction modeling of aneurysmal conditions with high and normal blood pressures. Comput. Mech. 38: 482-490 [online], 2006 [retrieved on MAy 20, 2011]. Retrieved from the Internet<URL:www.tafsm.org/PUB_PRE/jALL/j137-CM-HBP.pdf>.*

Tamer Hassan, Masayuki Ezura, Eugene V. Timofeev, Teiji Tominaga, Tsutomu Saito, Akira Takahashi, Kazuyoshi Takayama, and Takashi Yoshimoto; Computational Simulation of Therapeutic Parent Artery Occlusion to Treat Giant Vertebrobasilar Aneurysm Hassan et al.; AJNR Am J Neuroradiol 25: pp. 63-68, Jan. 2004; Others; 2004;.

Marcelo A. Castroa, Christopher M. Putmanb, Juan R. Cebral; Effects of Parent Vessel Geometry on Intraaneurysmal Flow Patterns Castroa et al.; Medical Imaging 2006: Physiology, Function, and Structure from Medical Images, edited by Armando Manduca, Amir A. Amini, Proc. of SPIE vol. 6143, pp. 123-131; Others; 2006;.

Tamer Hassan, Eugene V. Timofeev, Masayuki Ezura, Tsutomu Saito, Akira Takahashi, Kazuyoshi Takayama, and Takashi Yoshimoto; Hemodynamic Analysis of an Adult Vein of Galen Aneurysm Malformation by Use of 3D Image-Based Computational Fluid Dynamics Hassan et al.; AJNR Am J Neuroradiol 24: pp. 1075-1082, Jun./Jul. 2003; Others; 2003;.

David A. Steinman, Jaques S. Milner, Chris J. Norley, Stephen P. Lownie, and David W. Holdsworth; Image-Based Computational Simulation of Flow Dynamics in a Giant Intracranial Aneurysm Steinman et al.; AJNR Am J Neuroradiol 24: pp. 559-566, Apr. 2003; Others; 2003;.

Juan R. Cebral, Marcelo A. Castro, Christopher M. Putman; A Study of the Hemodynamics of Anterior Communicating Artery Aneurysms Cebral; Medical Imaging 2006: Physiology, Function, and Structure from Medical Images, edited by Armando Manduca, Amir A. Amini, Proc. of SPIE vol. 6143, No. 166C, pp. 166-175; Others; 2006;.

C. Karmonik, A. Mantha, C. M. Strother, G. Benndorf, R. Metcalf; Dynamic Pressure at Sites of Virtually Removed Paraclinoid Aneurysms: A Computational Fluid Dynamics Study Karmonik et al.; Medical Imaging 2006: Physiology, Function, and Structure from Medical Images, edited by Armando Manduca, Amir A. Amini, Proc. of SPIE vol. 6143, pp. 197-205; Others; 2006;.

Masaaki Shojima, Marie Oshima, Kiyoshi Takagi, Ryo Torii, Motoharu Hayakawa, Kazuhiro Katada, Akio Morita, Takaaki Kirino; Magnitude and Role of Wall Shear Stress on Cerebral Aneurysm Computational Fluid Dynamic Study of 20 Middle Cerebral Artery Aneurysms Shojima et al.; Stroke. 2004; vol. 35, No. 11, pp. 2500-2505; Others; 2004;.

Invention Disclosure citing listed references, Dec. 8, 2006, pp. 1-7.
Letter—Linder Blaumeier, Oct. 28, 2010, pp. 1-2.

* cited by examiner

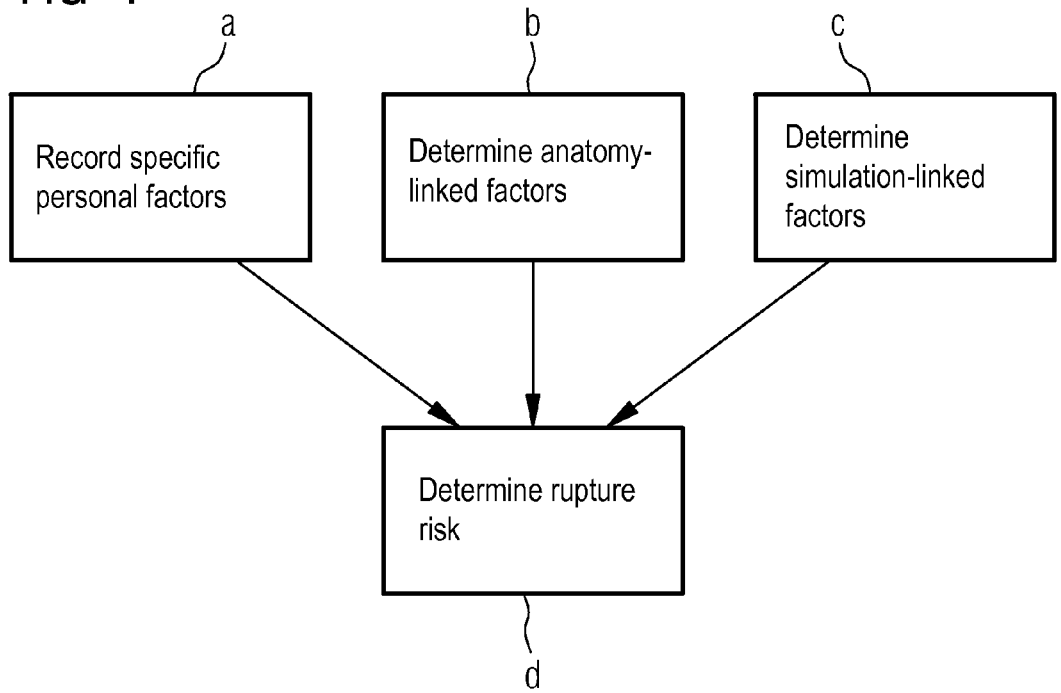
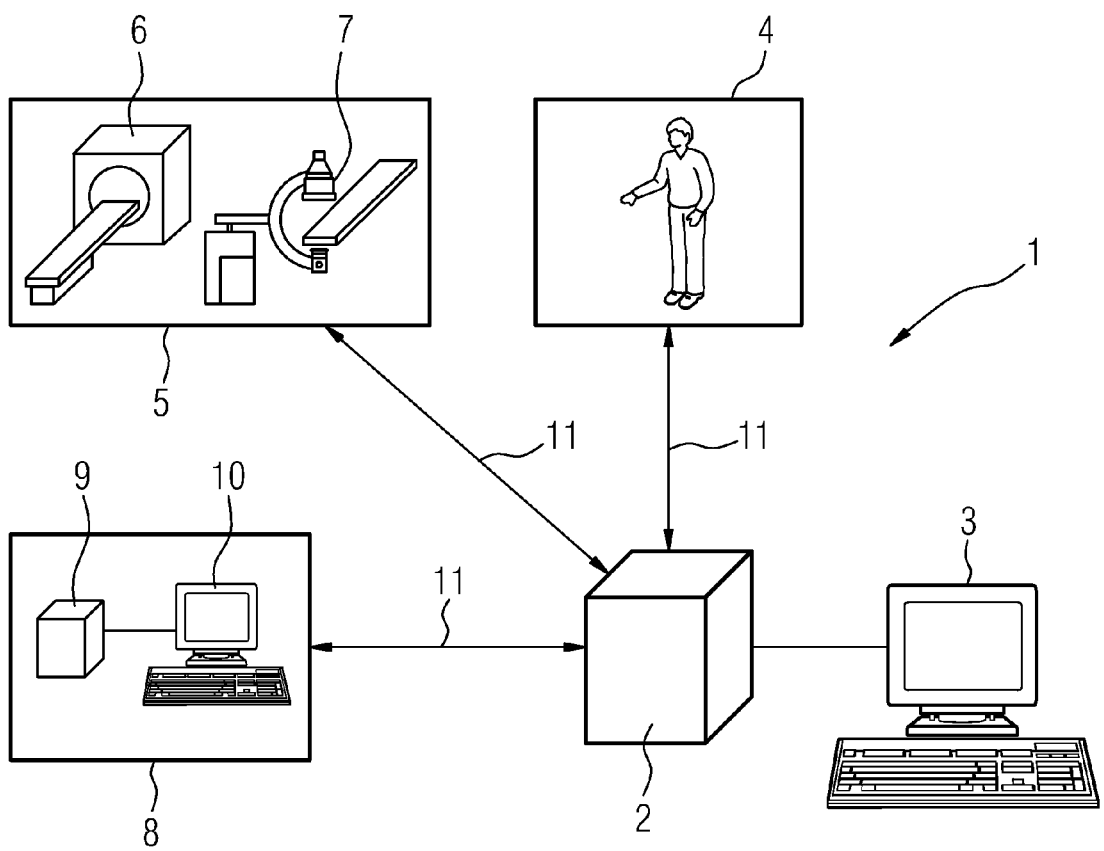

METHOD FOR ASSESSING A RUPTURE RISK OF AN ANEURYSM OF A PATIENT AND ASSOCIATED SYSTEM

CROSS REFERENCE TO RELATED APPLICATIONS

This application claims priority of German application No. 10 2007 026 519.2 filed Jun. 8, 2007, which is incorporated by reference herein in its entirety.

FIELD OF THE INVENTION

The invention relates to a method for assessing a risk of a rupture of at least one aneurysm of a patient as well as to an associated system.

BACKGROUND OF THE INVENTION

Aneurysms are spindle-shaped or sack-shaped localized permanent expansions of the cross-section of arterial blood vessels which occur as a result of congenital or acquired changes of the vessel wall. With what are referred to as true aneurysms (aneurysm verum) the entire diseased vessel wall is expanded, whereas with false aneurysms (aneurysm falsum or spurium) the cause lies in a split in the vessel wall. Aneurysms represent a significant risk for the patient, since in the case a rupture (i.e. a tearing outwards or inwards of the aneurysms) serious damage which may even be fatal can occur.

As a rule the causes of aneurysms are degenerative diseases of the vessel wall, in rare cases traumas, infections such as rheumatic fever, inflammations or a congenital weakness of connective tissue (Marfan syndrome, Ehlers-Danlos syndrome). In around 5 to 7% of aneurysms, these occur at multiple different places in the body. Aneurysms of the aorta can be of clinical significance not just for adults but also as a result of a Marfan syndrome or as late effects of a volume stress of the aorta with congenital heart defects with right-left shunt or a shunt-dependent perfusion of the lungs. Furthermore diseases in the Kawasaki syndrome can result in aneurysms on the coronary blood vessels.

To treat brain aneurysms there is the option of an endovascular or a neurosurgical treatment. In an endovascular therapy so-called coils, which involve spirals made of a platinum alloy, are brought into the aneurysm sack. These fill about 30% of the aneurysm and cause the formation of a thrombosis which prevents further blood circulation in the aneurysm. This means that a rupture, i.e. a tearing away, is no longer possible. In addition many further forms of therapy are possible, e.g. gluing etc.

With neurosurgical therapy on the other hand, which requires an open operation on the brain, the aneurysm is treated within the framework of a craniotomy. The aneurysm sack is clamped off with the aid of a clip, made of Titanium for example. In this way the aneurysm is cut off from the blood circulation. Alternatively the aneurysm can be wrapped, meaning that the artery aneurysm wall is strengthened.

The aneurysms which arise for example from a congenital weakness of the cells of the vessel inner wall (endothel cells) preferably occur at branches in vessels. Since at the intracranial arteries the muscle layer is thinner than at the other arteries of the body, the brain base vessels are predisposed to the occurrence of aneurysms. In autopsies aneurysms which have not bled are found in around 1 to 5% of the population. In women they occur more frequently than in men.

Aneurysms at the brain base vessels can cause fatal bleeding in they brain if they rupture. In such a case mortality rates are around 60 to 70%. In addition it is extremely probable that after such bleeding in the brain neurological incapacities such as paralysis, loss of speech and brain damage remain.

Therefore it is unavoidable in many cases that an aneurysm is treated, in order not to expose the patient to the danger of a rupture, i.e. a tearing of the aneurysm, with the consequences described. Intervening with an aneurysm however represents an intervention fraught with risk which is not induced with "stable" aneurysms and thus represents a danger without medical benefit for the patient. In addition such interventions are associated with high costs.

Thus the risk of such an intervention must be carefully balanced against the danger. In order to enable the decision for or against an intervention to be made, it is of greatest interest to be able to recognize the danger of rupture for an aneurysm, in order to be able to include this as a basis for making the decision.

It is currently the case that all aneurysms that have exceeded a certain threshold value of their diameter are treated. In addition anatomical circumstances are considered to a slight extent. The actual risk of rupture can only be assessed very inexactly on the basis of this data.

SUMMARY OF THE INVENTION

The object of the invention is thus to specify a method for assessing a risk of rupture of an aneurysm of a patient which is improved in this respect.

To achieve this object a method for assessing a risk of rupture of at least one aneurysm of a patient is provided, which is characterized by the risk of rupture being assessed by a computer device based on at least one specific personal factor for the patient and at least one relevant anatomy-linked factor relating to the anatomy and with reference to at least one simulation-linked factor determined by at least one simulation carried out by means of the and/or a further computing device and based on anatomical data for the at least one aneurysm.

In accordance with the invention the risk of a rupture is thus assessed or calculated from a combination of three different types of factor. Thus, to assess the risk of a rupture, it is not just the diameter of the aneurysm and a small amount of information about the anatomical circumstances that are determined, as was previously the usual procedure, but the rupture risk in accordance with the invention depends on personal factors, anatomy-linked factors and additionally on simulation-linked factors.

There are thus three different types of factor included in the assessment of the rupture risk, with the personal factors being factors which are specific to the respective patient, such as their age for example. Anatomy-linked factors are factors which can be determined in the area of the aneurysm or in a smaller or greater area surrounding it (which may be the whole body of the patient) as data for the prevailing anatomical circumstances, and which relate to the aneurysm in some form. As a rule the anatomical or anatomically-linked factors involve factors such as those able to be obtained with the support of imaging from recording images in the area of the aneurysm. Such a factor can for example be the aneurysm diameter. These are included to supplement the personal factors, with one or more factors of the respective type being able to be considered.

At least one simulation-linked factor is considered as a third factor in assessment of the risk. Such a simulation-linked factor is information or a number of data items which are computed within the framework of a simulation on the computing device or a further computing device of which the data is transmitted to the computing device for assessing the rupture risk. This involves a computer simulation, which is based on anatomical data from images for example, typically on rotation angiography images of the anatomy of the patient in the area of the aneurysm. In such cases for example a simulation of the blood flow in the aneurysm and/or an adjacent area of the vessel or in the vessel system overall can be conducted, in order thus to be able to obtain information on the basis of the flow behavior, about the risk of a rupture. As a rule physical variables, e.g. the flow speed, are computed within the framework of such a simulation.

The individual factors or factor types, which are incorporated inventively in the assessment of the rupture risk, are stored on the computing device that calculates said factors or are entered into this device or transmitted to it before the computation. In many cases this directly or indirectly involves physical, chemical or physiological data. If necessary the method can also be executed so that the computing device receives the command to determine the rupture risk for example by starting corresponding software, at which point it automatically accesses the data that it requires for this, where necessary with operator support. This means for example that the computing device requests specific factors from other computers, for which corresponding access authorizations are to be granted. This can be done over a network, for example within the context of accessing a patient database system of a clinic or such like.

According to the invention the general blood pressure of the patient and/or at least one existing disease, especially a vascular disease, and/or the age and/or a general state of health of the patient, can be used as the at least one personal factor.

As a rule it is advantageously possible to have many (relevant) personal factors of one type included in the assessment of the rupture risk, to allow the most accurate and individual possible risk assessment tailored to the patient to be undertaken. Accordingly further personal risk factors not specified here can be taken into account. Similar cases in the family of the patient and such like can for example also be considered as risk factors.

The blood pressure as general blood pressure plays a part insofar as the risk of a rupture increases with higher blood pressure. This risk is thus increased if hypertension is already present. Furthermore vascular diseases such as arteriosclerois are to be taken into consideration, caused or exacerbated for example by nicotine misuse. In addition the age and the general state of health of the patient obviously play a role.

A diameter of the aneurysm and/or the ratio of the aneurysm volume to the opening of the aneurysm neck and/or a growth tendency of the aneurysm and/or at least one inflow circumstance in the area of the aneurysm neck can be used as at least one anatomical factor.

For example the risk of rupture will thus be assessed as a function of the cross diameter of the aneurysm. This diameter is calculated as $$d=(a+b)/2,$$

with a being the larger or largest axis of the aneurysm and b the smaller axis of the aneurysm. In such cases the rule applies that the greater is the diameter of the aneurysm, the higher is the risk of a rupture. This results from Bernoulli's law, according to which, as the width of the vessel increases and the flow speed (of the blood) associated with it decreases, the pressure on the vessel wall increases.

Furthermore the ratio of the aneurysm volume to the opening of the aneurysm neck has a role to play. Also the growth tendency of the aneurysm, or with a number of aneurysms, the growth tendency of a plurality of aneurysms is to be taken into account. In this case for example, the rate of increase of the aneurysm in specific defined periods of time (in which for example control images are produced) is of significance. The risk of rupture is thus higher, the greater the growth of the aneurysm is. A measurement of the aneurysm can be undertaken in follow-up examinations at fixed or variable intervals.

The curve of the vessel can be taken into account as an inflow condition before the aneurysm neck for example.

With these anatomical or image-supported factors it is also of advantage for as many factors as possible or at least as many significant factors as possible to be included in the calculation of the rupture risk, in order to be able to specify said risk as accurately as possible.

A pressure on a surface of a vessel and/or a wall shear stress and/or at least one local and/or temporal gradient of a wall shear stress and/or a pressure distribution and/or the blood flow and/or at least one blood flow speed can be used as the at least one simulation-linked factor.

Also considered as simulation-linked factors are further factors not mentioned here, provided such factors can be determined within the framework of a simulation (on a computing device) and exhibit a relationship to the aneurysm.

The simulation factors, for example the wall shear stress, are obtained for example by the patient-specific anatomy, on the basis of three-dimensional images, being provided with a tool which as a program means conducts simulations on this basis and delivers the desired results, e.g. as physical data. Thus, as well as pressure on the vessel surface or the wall of the aneurysm e.g. a series of local or temporal gradients, for example for the wall stress and the pressure distribution, as well as the blood flow or the blood flow speed, can be determined.

Inventively at least one simulation-linked factor can thus be determined by a program means, especially by a program means stored on the computing device and/or a program means of a further computing device made available to this for access.

A program means can thus be used which is installed directly on the computing device as a single program or as a program package and which assesses the risk of rupture, or a means can be used which is stored on an external computing device, which is available to the first computing device for access. If necessary the results of the simulation can be transmitted directly by the program means to the computing device for computation of the rupture risk or can be requested by the latter. The software tool thus returns results to the computing device and said results are subsequently included as simulation-linked factors in the computation of the rupture risk, i.e. as a determined pressure distribution and such like for example.

To determine at least one simulation-linked factor, anatomical data for at least one aneurysm can be assessed by the computing device or a further computing device from at least one recorded image, especially by a program means. The simulation-linked factor is thus calculated or assessed with the aid of anatomical data or from such data. For this a suitable program means can be stored on the computing device or on an external computing device which undertakes this assessment. The anatomical data is thus for example incorporated into the assessment of the simulation-linked factor such that this serves as a basis for the assessment of the input data for the flow simulation or another simulation or from the input data itself. The anatomical data can be determined by an image processing algorithm, a segmentation for example.

The anatomical data is inventively determined from at least one image, if necessary from a number of images, for example by an averaging or by a combination of different information or by recording a fusion image.

At least one rotation angiography image and/or a computer tomography image and/or a magnetic resonance image and/or an ultrasound or sonography image can be used as the recorded image. If necessary fusion images or other combined images from different imaging techniques can be used the recorded images. Recorded images originating from other techniques not mentioned here can of course also be used for the assessment of the anatomical data.

Advantageously at least one simulation-linked factor is determined with reference to at least one flow simulation. Computational Fluid Dynamics in particular can be used. Computational Fluid Dynamics (CFD) is a fluid mechanics method in which numerical methods for problem solving are used. For example finite difference methods or finite element methods can be employed here.

Flow simulations allow simulation of the circumstances in the vessel system of the patient, especially in the area of the one or more aneurysms, in order in this way to obtain data which is of significance in answering the question as to whether the aneurysm is likely to rupture. For example the question of whether there is an especially high wall shear stress in particular wall areas of the aneurysm or whether an especially high pressure is acting on the surface and similar questions can be answered in this way. The simulation tools which are used in this case can be tools already known or tools developed explicitly for the case of calculating the flows in the vessel system or in the area of aneurysms.

At least one factor can be made available to the computing device using at least one program means, especially through entries made at a graphical user interface of the program means or a program means by a person who has access to at least one personal factor and/or at least one anatomically-linked factor and/or at least one simulation-linked factor, and/or at least one factor can be determined automatically by the computing device, especially by access to a database and/or a program means.

The procedure can also be such that the doctor or another person, with the aid of suitable software, obtains the relevant factors or data. This data is then made available as input factors for example to a software tool, which then assesses the rupture risk depending on these parameters or a subset of these parameters. Depending on the severity of the rupture risk, a more detailed decision for or against treatment of the aneurysms can be made.

A user interface of a program means is thus made available to the doctor or to another person entering data, into which the corresponding factors can be entered or which explicitly requests said factors. In such cases the person making the entries, depending on how the user prompts offered by the program are structured, can also be the patient himself or a technician given the task of calculating the risk of a rupture.

On the other hand the factors can be provided directly by a program means which is identical to the program means with the graphical user interface for entries or can be another program means. With a combination of the two methods the data is thus partly entered, partly provided directly by the program means. To this end the program means, after a request by an operator for example, accesses the corresponding factors, by requesting these from a database or from other programs or specific subroutines, for example from simulation programs, with which a flow simulation was conducted.

Accordingly the factors can also be at least partly (fully) automatically determined by the computing device, by for example the latter accessing a database with patient data (such as a hospital information system) and such like, in order for example to determine the age of the patient. Likewise the computing device can automatically access simulation programs, to which it passes the appropriate input data, at which point these programs perform the simulation and determine the required factors. The data can also be obtained with operator support or in the framework of letting a program of the program means run. Furthermore the factors for calculating the risk of a rupture can be returned automatically by specific program means for performing simulations and such like for example.

The risk of rupture can inventively be assessed by means of at least one program means stored on the computing device and/or at least one program means available for the device to access. The computing device thus has available (in a corresponding memory) a program means, which for its part can consist of different routines and can feature different subprograms or similar, with said program means knowing the calculation rules for the rupture risk (in the form of a corresponding implementation) and using this to enable the rupture risk to be assessed from the diversity of factors. Likewise the rupture risk can be assessed with the aid of a program means on an external computing device, to which the first computing device has access, or with a combination of local and external programs.

In particular the rupture risk can be assessed as a function of a weighting of the factors. This is based on the idea that the individual factors are of different importance for the rupture probability. For example the presence of specific diseases can be of differing significance for a rupture. Likewise it may be that the general state of health has less of an influence on the assessment of the rupture risk than for example the diameter of the aneurysm and such like. In this case the weighting can differ entirely from patient to patient, with database knowledge or knowledge of an expert system or also entries made by a doctor for example being able to be accessed for determination of the weighting factors.

A calculation specification for assessing the rupture risk depending on the factors can be determined within the framework of a patient-based study. This means that a study, especially of a number of patients, is conducted, which involves a mass screening in the clinical environment for example. This patient-based study, in which the patients are advantageously observed over a longer period, then for example delivers data relating to a correct weighting of the factors or in relation to the particular factors that can be usefully included in the calculation. For this a computing device can be provided with a suitable program means which receives the data of the mass screening or the study as input or requests such data automatically.

Above and beyond this the invention relates to a system for assessing a rupture risk of at least one aneurysm of a patient with a computing device, which is embodied to determine the rupture risk as a function of at least one specific personal factor specified for the patient and at least one anatomically-linked factor relating to the anatomy of the aneurysm and/or in the area of the at least one aneurysm and of at least simulation-linked factor calculated by means of at least one simulation performed by means of the and/or a further computing device and based on anatomical data for the at least one aneurysm, especially in accordance with a method as described above.

The system is thus characterized by different hardware and software components. Initially a computing device is available, with the aid of which, if necessary through a software tool, the rupture risk can be assessed or computed. To this end the computing device receives as its input anatomical factors, personal factors and simulation-linked factors. These factors are for example acquired automatically by the computing device from a database (e.g. a patient database). Other factors are entered by a doctor or by a scientist given the task of calculating the rupture risk. Furthermore the factors can be determined from flow simulations running on the computing device and if necessary started fully automatically by the software tool.

These types of simulations can furthermore be assessed on other computing devices which are present in the system as extra devices in addition to the first computing device (and are external or not local to this device). These computing devices then return the results on request or automatically to the (first) computing device for assessing the rupture risk. If necessary the system can also feature a image recording device with which images are recorded for example to determine anatomy-linked factors or anatomical data as a basis for the required simulations.

This means that it is possible to assess the rupture risk within the framework of a technical (measurement) data evaluation including taking account of the numerous relevant dependencies. This actually excludes a doctor having to arrange an intervention or to conduct one himself, although this is clinically not induced, so that the invention can be prevented from subjecting a patient without benefit to an unnecessarily high risk at high cost. It also prevents an intervention being rejected or refused by a doctor although this would be clinically induced. Also prevented is the case in which the doctor subjects the patient to a situation in which the aneurysm can rupture at any time, with such a rupturing of the aneurysm having the serious consequences outlined above. It is thus possible, through the inventive rupture risk assessment or the system provided for this purpose, to make a more detailed decision in favor of or against an intervention.

BRIEF DESCRIPTION OF THE DRAWINGS

Further advantages, features and details of the invention emerge with reference to the following exemplary embodiments as well as from the figures. The figures show:

FIG. 1 a chart for performing an inventive assessment of a rupture risk of an aneurysm, FIG. 2 an inventive system for assessing a rupture risk, FIG. 3 to 5 examples for determination of anatomy-linked factors from rotation angiography imaging, FIGS. 6 and 7 examples of anatomical data for use in the determination of simulation-linked factors and FIGS. 8 and 9 diagrams of a spatial distribution of a wall shear stress at different points in time.

DETAILED DESCRIPTION OF THE INVENTION

Figure 3:
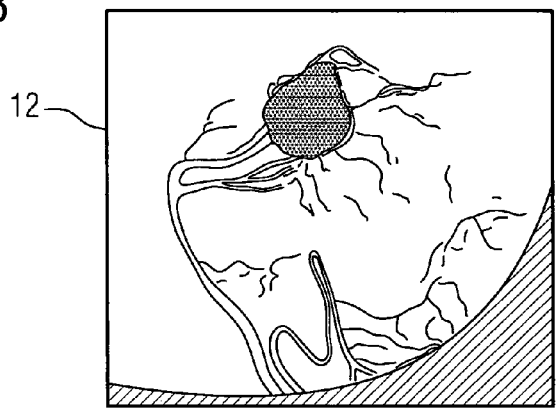

FIG. 1 shows a chart for carrying out an inventive assessment of a rupture risk of least of one aneurysm.

In this figure, specific personal factors are recorded in accordance with box a for the patient having the aneurysm or the number of aneurysms. Furthermore, in accordance with box b, anatomy-linked factors are determined or retrieved by a computing device for assessing the rupture risk which relate to the anatomy in the area of the aneurysm (thus for example the shape of the aneurysm itself or the circumstances in the inflow area and such like). In accordance with box c simulation-linked factors are also taken into account, these having been determined within the framework of at least one simulation relating to the aneurysm or to the number of aneurysms. As a rule this involves data from flow simulations, in order for example to determine the blood flow speed and local or temporal gradients for the wall shear stress or a pressure distribution and such like.

These different factors in accordance with boxes a, b and c are all included in the assessment of the rupture risk in accordance with box d. The rupture risk is also determined as a function of three different types of factor, namely personal, anatomy-linked and simulation-linked factors. In such cases the factor groups can again provide a plurality of individual factors for rupture risk assessment. The rupture risk assessment can thus be carried out precisely as a function of a corresponding calculation to any degree of accuracy. The calculation specification on which the assessment is based is expediently determined for this purpose in advance within the framework of a medical study or a number of clinical studies and is determined from empirical values and such like. This effectively prevents interventions being performed unnecessarily on a patient or on the other hand not being carried out although these are induced.

FIG. 2 shows an inventive system 1 for assessing the risk of a rupture. The system 1 comprises a computing device 2 which is embodied for assessing the rupture risk from the individual factors. To make it possible for the user to enter data or for output of the results a display screen 3 with an associated keyboard is also provided. Further operating aids such as a mouse for the screen 3 or the computing device 2 are not shown here, but can likewise be a component of the system 1.

So that an assessment of the rupture risk is possible using the computing device 2, personal data is entered into this device as personal factors 4. If necessary these personal factors 4, which relate to the patient with the one or more aneurysms can already be stored on the computing device 2 or the latter can have retrieved these factors via a data connection from another computing device (of the system or external).

Furthermore the computing device 2 will also be supplied with anatomy-linked factors 5, which for example relate to anatomy-linked factors 5 determined using a magnetic resonance tomography device 6 or an x-ray device 7, for which purpose appropriate images have been created with these devices, showing the aneurysm or an area surrounding the aneurysm or the number of aneurysms. These anatomy-linked factors 5 are likewise directed to the computing device 2.

Simulation-linked factors 8, which the computing device 2 likewise receives as input, originate from a further computing device 9 with an assigned screen 10 with an input device.

In other exemplary embodiments the simulation-linked factors can at least partly be already present integrated into the computing device 2, for example for a simulation conducted directly by the computing device 2 with the screen 3 itself. Likewise, instead of two computing devices 2, 9 a single computing device can be provided.

The different factors 4, 5 and 8 are if necessary requested explicitly by the computing device 2 for example from the magnetic resonance device 6 and if necessary only determined within the framework of an evaluation by the computing device 2 from image data or other original data with the aid of program means embodied for this purpose. Where necessary the data can be entered via the screen 3 or requested by the computing device 2 from databases and such like. As a rule different options will be used for acquiring factors 4, 5 and 8, as indicated in this figure by the double arrows 11.

Thus, in the exemplary embodiment shown, there is an active request for factors 4, 5 or 8 as well as an automatic provision of the individual factors to the computing device 2.

However systems are also conceivable in which data is only actively requested or only automatically supplied to a computing device.

With the aid of a calculation specification available to the computing device 2 or, as is the case here, stored on the device, a program means implemented on the computing device 2 can assess the rupture risk taking into account weighting specifications for the individual factors 4, 5 and 8.

Figure 4:
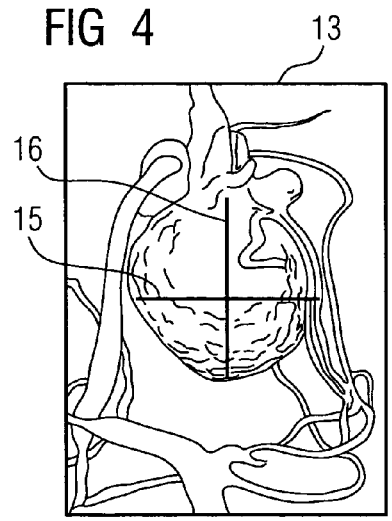
Figure 5:
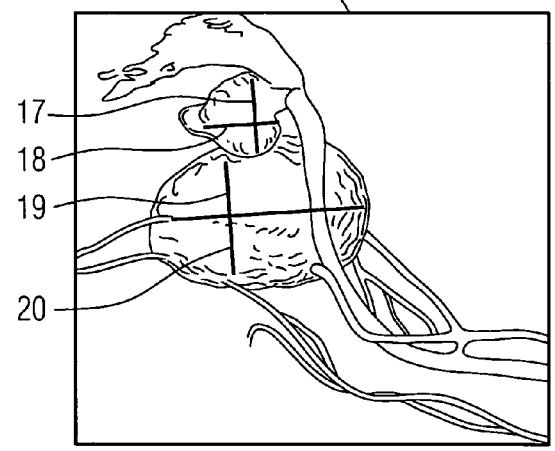

FIGS. 3 to 5 show examples for determining anatomy-linked factors from rotation angiographic images 12, 13 and 14.

The rotation angiographic images 12, 13 and 14 in this case show aneurysms or the surrounding area of aneurysms. The relevant anatomical or image-based factors for assessing the rupture risk are established from the rotation angiographic images 12, 13 and 14 with the aid of a suitable image processing means (program means), for example the length of the axes 15, 16, 17, 18, 19 and 20 in the rotation angiographic images 13 and 14. From the lengths of axes 15 to 20 for example, the cross diameter of the respective aneurysm can be determined, which is calculated from the total of the lengths of the longest axes of the aneurysm and the length of the shorter axis of the aneurysm, divided by 2. This anatomical factor is included in the assessment of the rupture risk in this case, in such a way that, the greater is the diameter which was determined in this manner, the higher the rupture risk is to be set.

Further anatomical factors not shown in any greater detail here, which can be determined with the aid of rotation angiographic imaging 12 to 14, are for example the ratio of the aneurysm volume for opening the aneurysm neck or the growth tendency, for which purpose rotation angiographic images must be produced for comparison at specific intervals.

Thus anatomical factors which are of significance for assessing the rupture risk can be determined on the basis of recorded images such as rotation angiographic images 12 to 14.

Figure 6:
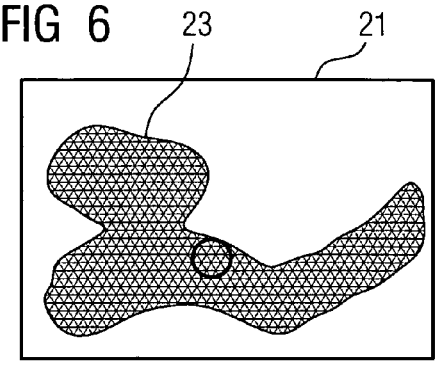
Figure 7:
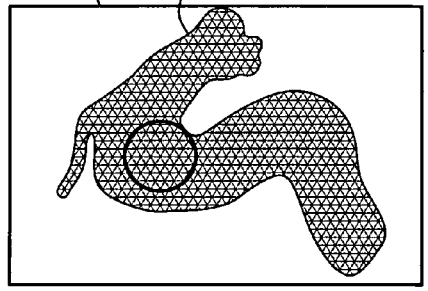

FIGS. 6 and 7 show examples for anatomical structures 21 and 22 for use in the determination of simulation-linked factors. In this case recorded images are used as a basis, for example rotation angiographic images as are shown in FIG. 3 to 5, which are subsequently put into a suitable format to enable them to be used directly or indirectly as input data. in the present case the anatomical structures 21 or 22 of FIG. 6 or 7 have been processed into networks of triangles 23 or 24, meaning that they are available in a format which a system for carrying out a flow simulation for determining the simulation-linked factors which can be taken into account during rupture risk calculation. In general other formats can of course also be used. It is only a matter of the format concerned being one on which a simulation can be performed.

Figure 8:
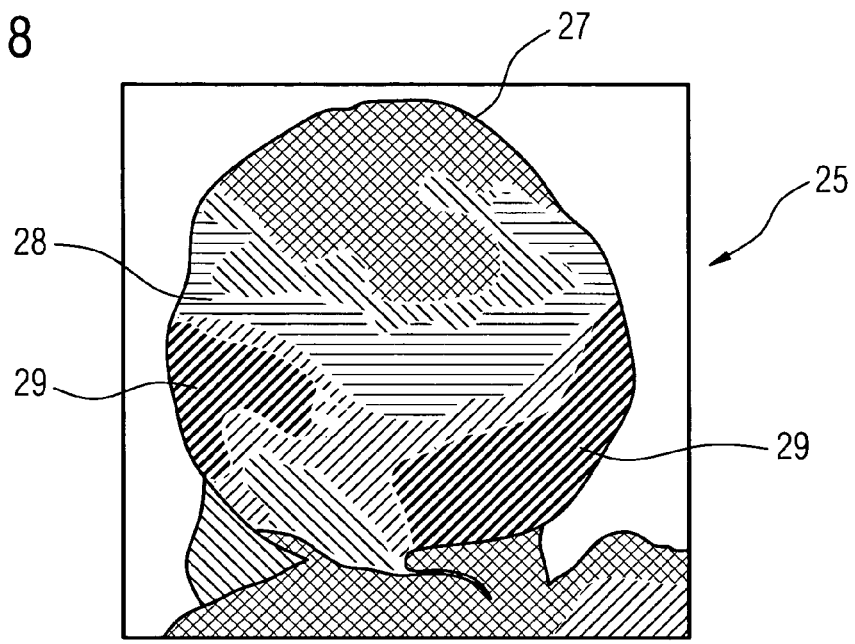
Figure 9:
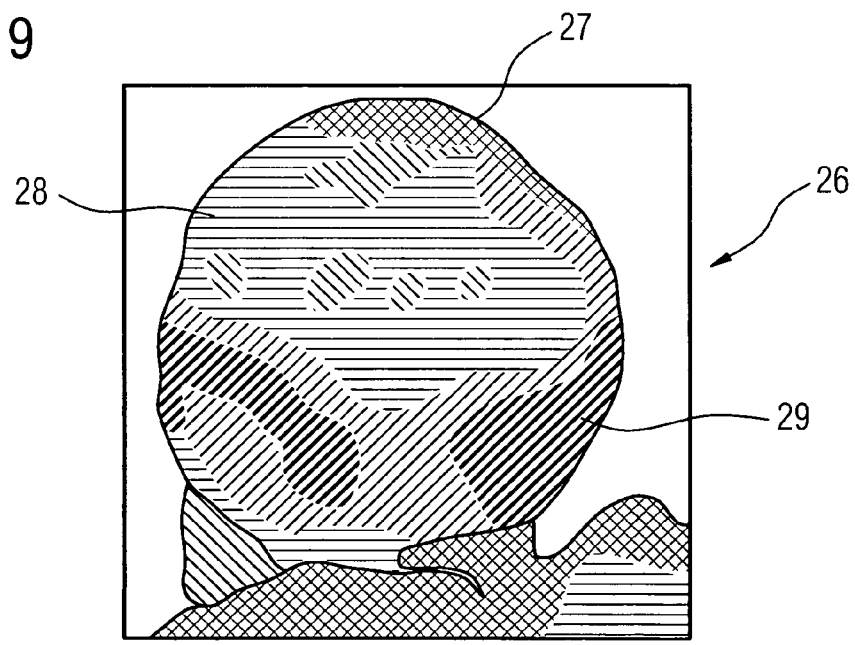

Finally, in FIGS. 8 and 9 diagrams 25 and 26 show a spatial distribution of a wall shear stress as a simulation result at different points in time for an aneurysm 27. In these figures the brighter areas 28 in a thermal diagram (which are only distinguished here from the darker areas in the type of shading) of the aneurysm 27 indicate the area in which a higher wall shear stress is present, whereas the darker areas 29 stand for areas of the aneurysm 27, at which at the given point in time of the respective images 25, 26 a lower wall shear stress is active. With the wall shear stresses determined in this way further factors are thus present which can be includes as simulation-linked factors for calculating the rupture risk by the computing device.

The invention claimed is:

1. A method for assessing a rupture risk of an aneurysm of a patient, comprising:
   computing the rupture risk by a computing device depending on:
      a personal factor specific to the patient,
      an anatomy-linked factor related to an anatomy of the aneurysm, and
      a simulation-liked factor related to the aneurysm,
   wherein the rupture risk is assessed as a function of a plurality of different weightings respectively related to the personal factor, the anatomy-linked factor, and the simulation-linked factor.

2. The method as claimed in claim 1, wherein the personal factor is selected from the group consisting of: a blood pressure, an existing disease, a vascular disease, age, and a general state of health.

3. The method as claimed in claim 1, wherein the anatomy-linked factor is selected from the group consisting of: a diameter of the aneurysm, a ratio of aneurysm volume to opening of aneurysm neck, a growth tendency of the aneurysm, and an inflow condition in an area of the aneurysm neck.

4. The method as claimed in claim 1, wherein the simulation-linked factor is selected from the group consisting of: a pressure on a surface of a vessel, a wall shear stress of the aneurysm, a local gradient of the wall shear stress, a temporal gradient of the wall shear stress, a pressure distribution of the aneurysm, a blood flow, and a blood flow speed.

5. The method as claimed in claim 1, wherein the simulation-linked factor is determined by a computer program.

6. The method as claimed in claim 1, wherein the simulation-linked factor is determined based on the anatomy of the aneurysm from a recorded image of the aneurysm.

7. The method as claimed in claim 6, wherein the recorded image is selected from the group consisting of: a rotation angiography image, a computer tomography image, a magnetic resonance device image, and an ultrasound image.

8. The method as claimed in claim 1, wherein the simulation-linked factor is determined based on a flow simulation.

9. The method as claimed in claim 1, wherein the personal factor, the anatomy-linked factor, or the simulation-linked factor is provided by a user input, or by a program, or by an automatic calculation.

10. The method as claimed in claim 1, wherein a calculation specification for assessing the rupture risk is determined as a function of the personal factor, the anatomy-linked factor, and the simulation-linked factor within a framework of a patient-related study.

11. The method as claimed in claim 1, wherein the plurality of different weightings are determined based on a plurality of different influences of the respectively related personal factor, anatomy-linked factor, and simulation-linked factor for the rupture risk.

12. A system for assessing a rupture risk of an aneurysm of a patient, comprising:
   a computing device that computes the rupture risk depending on:
      a personal factor specific to the patient,
      an anatomy-linked factor related to an anatomy of the aneurysm, and
      a simulation-liked factor related to the aneurysm,
   wherein the rupture risk is assessed as a function of a plurality of different weightings respectively related to the personal factor, the anatomy-linked factor, and the simulation-linked factor.

* * * * *